(12) United States Patent
Fluhrer et al.

(10) Patent No.: US 6,266,553 B1
(45) Date of Patent: Jul. 24, 2001

(54) SPIRAL SCANNING COMPUTED TOMOGRAPHY APPARATUS, AND METHOD FOR OPERATING SAME, FOR CARDIAC IMAGING

(75) Inventors: Manfred Fluhrer, Hallerndorf; Klaus Klingenbeck-Regn, Nuremberg; Andreas Lutz, Poxdorf; Judith Regn, Nuremberg, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/151,588

(22) Filed: Sep. 11, 1998

(30) Foreign Application Priority Data

Sep. 12, 1997 (DE) .............................. 197 40 214

(51) Int. Cl.$^7$ ...................................... A61B 5/05
(52) U.S. Cl. .......................... 600/428; 600/481; 600/483; 600/508; 600/509; 600/513; 600/521; 600/546; 378/21; 378/62; 378/145; 378/146; 378/150; 378/162
(58) Field of Search ..................................... 600/373, 374, 600/407, 425, 427, 436, 481, 483, 508, 509, 513, 521, 546, 428; 378/13, 14, 15, 21, 22, 23, 27, 28, 31, 62, 69, 135, 145, 150, 162, 8

(56) References Cited

U.S. PATENT DOCUMENTS

| | | | |
|---|---|---|---|
| 4,182,311 | * | 1/1980 | Seppi et al. ........................... 600/428 |
| 4,547,892 | * | 10/1985 | Richey et al. ........................... 378/8 |
| 4,868,747 | * | 9/1989 | Mori et al. ........................... 382/131 |
| 5,262,946 | * | 11/1993 | Heuscher ............................... 378/15 |
| 5,383,231 | * | 1/1995 | Yamagishi ............................. 378/15 |
| 5,800,355 | * | 9/1998 | Hasegawa ............................. 600/436 |

* cited by examiner

Primary Examiner—Marvin M. Lateef
Assistant Examiner—Jeoyuh Lin
(74) Attorney, Agent, or Firm—Schiff Hardin & Waite

(57) ABSTRACT

In a computed tomography apparatus, and a method for operating same, for obtaining cardiac images, a spiral scan of a measurement volume containing a patient's heart is conducted, the production of the scanning data during the spiral scanning being synchronized with an ECG signal from the patient, in order to produce a graphic representation of the examination volume, and thus an image of the patient's heart. The ECG signal is employed to control the generation of the data during the spiral scanning at phase of the cardiac cycle wherein minimum movement of the heart takes place. The chronological correlation between the recording of the scanning data and the ECG signal is fixed, so that within each number of successive time intervals, a dataset is obtained completely within that time interval. The datasets from the successive time intervals are then combined to produce an image of the heart. Since the component images are all obtained in a low-motion phase of the heart, the resulting overall image is particularly sharp.

14 Claims, 2 Drawing Sheets

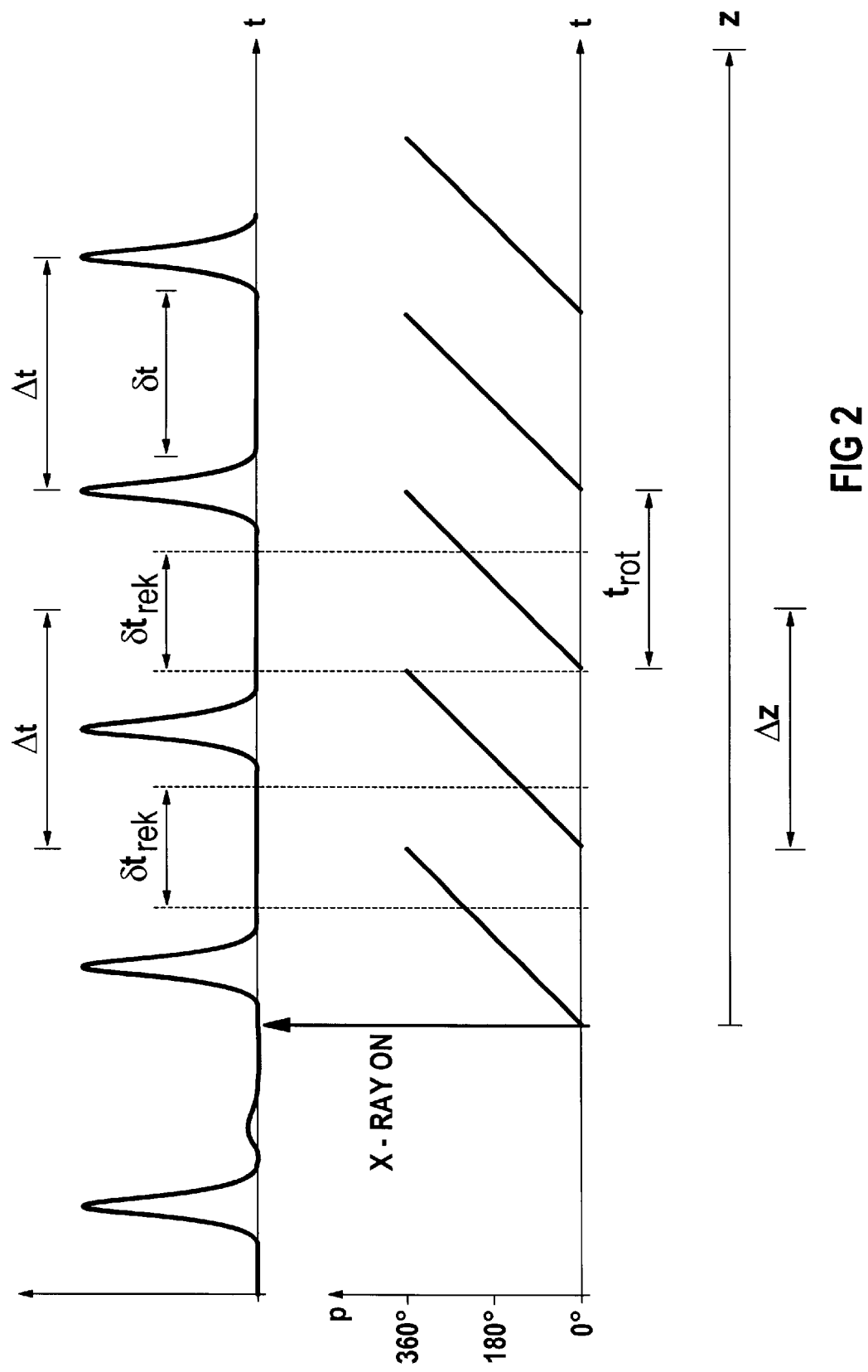

SPIRAL SCANNING COMPUTED TOMOGRAPHY APPARATUS, AND METHOD FOR OPERATING SAME, FOR CARDIAC IMAGING

SPECIFICATION

BACKGROUND OF THE INVENTION

1. Field of the Invention

The present invention is directed to a computed tomography apparatus operable in a spiral scanning mode for obtaining an image of a patient's heart, as well as to a method for operating such a computed tomography apparatus for obtaining cardiac images.

2. Description of the Prior Art

It is known to conduct helical or spiral scanning of a patient, using a computed tomography apparatus, by causing the measurement unit consisting of the X-ray source and the detector to continuously rotate while displacing the patient bed along its longitudinal direction (z-direction). From the detector data, volume data of the subject of examination can be obtained using an image computer.

Movements of the organs, in particular of the heart, can lead to motion artifacts in the image produced from the volume data, due to the relatively long scan time.

U.S. Pat. No. 4,182,311 describes a method for computed tomography of the heart which does not make use of spiral scanning. In parallel with the scanning of the heart, the ECG signal is recorded. On the basis of the ECG signal, those projections are selected that correspond to a particular phase of the heart action. These projections, associated with various projection angles, are combined to form a dataset that allows the reconstruction of an image.

In U.S. Pat. No. 5,383,231 a method is described for spiral scanning of the heart by means of a computed tomography apparatus, in which, in a manner analogous to the method of U.S. Pat. No. 4,182,311, projections associated with various projection angles and/or various revolutions of the measurement system, and which reproduce the same phase of the heart action, are combined to form datasets that allow the reconstruction of CT images, in particular three-dimensional CT images.

In both cases, an improvement is achieved in comparison to tomographic examinations of the heart that take place without taking into account the ECG signal; however, sufficiently sharp images still are not produced.

SUMMARY OF THE INVENTION

An object of the present invention is to provide a computed tomography apparatus which is operable in a spiral scanning mode wherein a sharp imaging of the heart is achieved.

The above object is achieved in accordance with the principles of the present invention in a computed tomography apparatus having a measurement system for conducting a spiral scan of a measurement volume containing a patient's heart, wherein the production of scanning data obtained using the spiral scanning is synchronized with an ECG signal from the patient in order to produce a graphic representation of the examination volume, and thus an image of the patient's heart.

The ECG signal is not merely used as a periodic trigger, as is conventional in the above-described known systems, but instead is employed to control the generation of volumetric data during the spiral scanning at phases of the cardiac cycle wherein minimum movement of the heart takes place, i.e., in the diastole. The chronological correlation between the recording of the scanning data in the spiral scanning an ECG signal is fixed, such as by employing the "radiation on" signal for conducting the spiral scanning, so that within each of a number of successive time intervals, a dataset is obtained completely within that time interval, with the datasets from the successive time intervals then being combined to produce a low-motion image of the heart. Since all of the scanning data are obtained at times when the heart is in a low-motion phase, the resulting complete image is particularly sharp, in contrast to images produced employing conventional ECG triggering.

DESCRIPTION OF THE DRAWINGS

FIG. 2 shows curves for the explanation of the operation of the computed tomography apparatus according to FIG. 1.

DESCRIPTION OF THE PREFERRED EMBODIMENTS

Figure 1:
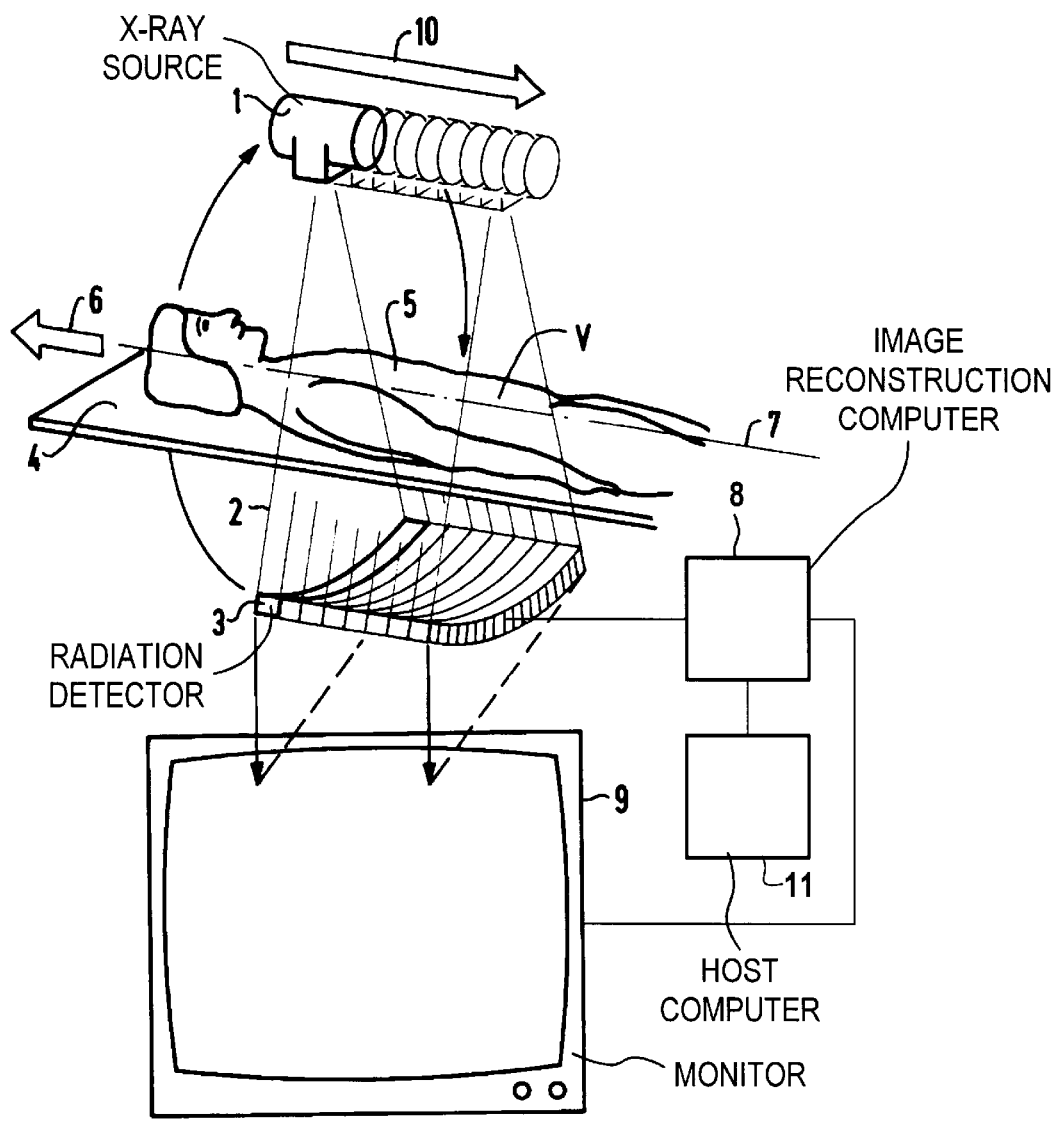
FIG. 1 shows the basic components of a computed tomography apparatus for spiral scanning of a patient constructed and operating in accordance with the invention

In FIG. 1, an X-ray source 1 is shown that emits a fan-shaped X-ray beam 2, which is incident on a beam detector 3 curved around the focus of the X-ray source 1 and formed by a series of detector elements. A patient bed 4 with a patient 5 thereon is located between the X-ray source 1 and the beam detector 3.

In order to scan a volume V of the patient 5, the patient bed 4 is displaced in the direction of the arrow 6 by predetermined advancement steps, while the measurement unit formed by the x-ray source 1 and the detector 3 rotates about the system axis 7. The scanning data (electrical signals) thereby produced by the detector elements of the beam detector 3 are supplied to an image reconstruction computer 8, which reconstructs, i.e. calculates, images of the patient therefrom, and reproduces these images on a monitor 9. These images are computed tomograms of the scanned volume. As an alternative to the displacement of the patient bed 4 in the direction of the arrow 6, for the scanning of a predetermined volume V of the patient 5 it is also possible to displace the measurement system in the direction of the arrow 10 while the patient bed 4 remains stationary.

As shown in FIG. 2, the ECG signal of the patient is recorded in parallel with the spiral scanning. The upper curve represents in schematic form an ECG signal with a spacing between the R-peaks of $\Delta t$ (e.g. $\Delta t=1s$ for 60 heart beats per minute). The lower curve in FIG. 2 represents the spiral recording with a single-row scanner, represented by the periodic increasing of the projection angle $\phi$ from 0 to 360° as time progresses. The duration of a period thereby corresponds to the exposure time for a complete 360° rotation of the measurement system. Due to the continuous motion of the patient bed 4, in the spirals the axial z-position also increase in linear fashion in the direction of the system axis 7. For this reason, a corresponding z-axis is also shown next to the time axis in FIG. 2. The following is valid:

$$z = v \cdot t \qquad \text{Eq.(1)}$$

for a constant bed velocity v of the patient bed 4.

The ECG signal must be recorded and digitally stored by suitable means, e.g. a computer, preferably the host computer 11 of the computed tomography apparatus. In addition, the production of a chronological correlation between the ECG signal and the spiral scanning must take place in the storage means, e.g. by storing the initial time of the spiral scanning on the time axis relative to the ECG signal. This can, for example, be achieved by also supplying the "radiation on" signal of the computed tomography apparatus to this computer 11, and this is mixed in with the ECG signal in suitable form in isochronous fashion.

Under these circumstances, an ECG triggering, in contrast to the conventional ECG triggering, can take place as follows:

By mathematical analysis of the ECG signal in the computer 11, which also serves as an evaluation means, the individual R-peaks and their chronological spacings $\Delta t$ are determined. For simplicity, it is assumed that $\Delta t$ is constant, to a good approximation. If $\Delta t > t_{rot}$ (time for one revolution of the measurement unit, i.e., a sub-second scanner), a time interval $\delta t$ can be found between adjacent R-peaks, which falls into the diastole, representing a quiet phase of the heart, and within which low-motion images of the heart thus can be reconstructed. Since the chronological correlation between the recording of the scanning data obtained in the spiral scanning and the ECG signal is fixed (radiation on), at each time interval $\delta t$ a dataset obtained completely within the respective time interval $\delta t$ can then be selected, and on the basis thereof low-motion images of the heart can be reconstructed by the computer 8.

For illustration, assume an example with $t_{rot} = 0.75s$. A simplified reconstruction is assumed, without spiral interpolation, as a partial revolution reconstruction from 240°. For this, volumetric data from a time window of $\delta t_{rek} = 0.5s$ are then required.

Case 1:

Heart frequency of 60/min, corresponding to $\Delta t = 1s$. The time duration of the diastole is then approximately 70% of the RR spacing, i.e., $\delta t \leq 0.7s$. Since $\delta t_{rek} < \delta t$, given slightly irregular spacings of the R-peaks the time window $\delta t_{rek}$ can still be displaced within the diastoles in such a way that successive time windows are again located at equidistant time intervals $\Delta t$.

Case 2:

Heart frequency of 80/min, corresponding to $\Delta t = 0.75s$. Thus, $\delta t < 0.525s$. It is still true that $\delta t_{rek} < \delta t$, however, it is expected that corrective measures for irregularities of the heartbeat can no longer be carried out in practice.

For a single-row scanner with $t_{rot} = 0.5s$, the chronological relations are scaled correspondingly: $\delta t_{rek} = 0.33s$. The problem of a higher heart frequency is then accommodated in a satisfactory manner.

Also under the assumption that, as specified, 240° datasets in identical time intervals $\Delta t$ can be extracted from the overall dataset obtained in the spiral scanning, there is the risk that the overall heart image will not be acquired in gap-free fashion in the axial direction. This is because, by means of equation 1, a fixed axial spacing $\Delta z$ of adjacent images is associated with $\Delta t$. This risk can be prevented by suitable selection of the pitches during the spiral scanning. By definition, $v = p \cdot d / t_{rot}$ with slice thickness d and pitch p. From Equation 1, then:

$$\frac{\Delta z}{d} = p \cdot \frac{\Delta t}{t_{rot}} \quad \text{Eq. 2}$$

a gap-free or overlapping imaging requires that $\Delta z/d \leq 1$, and thus a corresponding limitation of the pitch:

$$p \leq \frac{t_{rot}}{\Delta t} \quad \text{Eq. (3)}$$

a) $\Delta t = 1s$, $t_{rot} = 0.75s$: $p \leq 0.75$
b) $\Delta t = 0.75s$, $t_{rot} = 0.75s$: $p \leq 1$
c) $\Delta t = 1s$, $t_{rot} = 0.5s$: $p \leq 0.5$
d) $\Delta t = 0.75s$, $t_{rot} = 0.5s$: $p \leq 2/3$ Thus, the faster the scanner rotates relative to the heart frequency, the smaller the maximum allowable pitch becomes.

For practical execution, these considerations indicate that before the scan an average heart frequency should be determined for each patient, and the pitch should be matched correspondingly during the exposure.

A computed tomography apparatus operating according to the above-described method has the following features.

1. Marking the beginning of the spiral in the ECG signal and setting of a pitch value, so that a gap-free imaging of the heart is achieved in the axial direction.
2. ECG recording in the computer and marking the beginning of the spiral on the time-axis of the ECG.
3. Identification of the diastoles and corresponding time window.
4. Obtaining spiral scan datasets at the time windows from 2.
5. Specific partial revolution reconstruction (240°) for minimization of the time window.
6. Selection of the pitch for spiral exposures, so that gap-free imaging of the heart is ensured.
7. Determination of the average heart frequency of a spiral scan, for the determination of the suitable pitch value.
8. Given an irregular heartbeat, adaptation of the time window for reconstruction, so that the images arise in equidistant time spacings and thus equidistant axial spacings.
9. Monitoring the heart frequency during the spiral exposure, and corresponding control of the speed of the bed displacement, so that the allowable pitch value is not exceeded.

The invention has been specified above in the context to the example of a single-row scanner, i.e. a computed tomography apparatus whose detector is formed by a single row of detector elements. The invention can also be used to particular advantage in multi-row scanners, i.e. a computed tomography apparatus whose detector is formed by several rows of detector elements, because, corresponding to the number of rows, the set of measurement data obtained between two R-peaks is greater than in a single-row scanner, and accordingly a gap-free axial scanning of the heart is more easily possible.

Instead of a computed tomography apparatus of the third generation, as in the described embodiment, the invention can also be used in fourth-generation tomography systems.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:
    means for conducting a radiological spiral scanning of an examination volume in which an examination subject is disposed, thereby obtaining spiral scan data;
    means for obtaining an ECG signal, containing R-waves, from a heart of a subject in said examination volume over a plurality of cardiac cycles, said ECG signal, consisting of periodic signal portions respectively representing only low-motion phases of the heart, each low-motion phase being disposed between two immediately successive R-waves in said ECG signal;

means for controlling the spiral scanning of said examination volume dependent on said ECG signal for obtaining said spiral scan data in a plurality of successive scanning datasets respectively obtained only during said low-motion phases; and means for producing images of the heart from said scanning datasets, with each image being produced using only one of said datasets respectively.

2. A computed tomography apparatus as claimed in claim 1 wherein said means for conducting a spiral scanning has a pitch value associated therewith, and wherein said spiral scanning is conducted around an axial direction, and wherein said means for controlling comprises means for setting said pitch value dependent on said ECG signal for obtaining a gap-free image of the heart in the axial direction.

3. A computed tomography apparatus as claimed in claim 1 further comprising storage means in said means for controlling for storing said ECG signal along a time axis, and means for marking a beginning of the spiral scanning on said time axis for correlating said spiral scanning with said ECG signal.

4. A computed tomography apparatus as claimed in claim 3 wherein said ECG signal stored in said storage means on said time axis exhibits a plurality of successive, predetermined time windows, and wherein said means for controlling said spiral scanning comprises means for obtaining said spiral scan data only during said time windows, with only one of said datasets being obtained per time window.

5. A computed tomography apparatus as claimed in claim 4 wherein said means for conducting spiral scanning comprises a radiation source, a radiation detector, and means for rotating said radiation source and said radiation detector around said examination volume in a plurality of successive revolutions, and wherein said means for controlling the spiral scanning comprises means for obtaining data in said time windows which are respectively portions of successive revolutions of said means for conducting a spiral scanning.

6. A computed tomography apparatus as claimed in claim 4 wherein said means for producing said overall image comprises means for producing said overall image from datasets obtained at equidistant time intervals.

7. A computed tomography apparatus as claimed in claim 1 wherein said means for conducting a spiral scanning includes a radiation source, a radiation detector, a patient bed on which an examination subject is disposed and means for rotating said radiation source and said radiation detector around an axis while advancing said patient bed along said axis at a bed speed, and wherein said means for conducting a spiral scanning has a pitch value associated therewith, and wherein said computed tomography apparatus further comprises means for monitoring a heartbeat frequency of the heart during said spiral scanning and for controlling said bed speed so that a predetermined pitch value is not exceeded.

8. A method for cardiac imaging using a computed tomography apparatus comprising the steps of:

conducting a radiological spiral scanning of an examination volume in which an examination subject is disposed, thereby obtaining spiral scan data;

obtaining an ECG signal, containing R-waves, from a heart of a subject in said examination volume over a plurality of cardiac cycles, said ECG signal consisting of periodic signal portions respectively representing only low-motion phases of the heart, each low-motion phase being disposed between two immediately successive R-waves in said ECG signal;

controlling the spiral scanning of said examination volume dependent on said ECG signal for obtaining said spiral scan data in a plurality of successive scanning datasets respectively obtained only during said low-motion phases; and producing images of the heart from said scanning datasets, with each image being respectively produced using only one of said datasets.

9. A method as claimed in claim 8 wherein the step of conducting a spiral scanning has a pitch value associated therewith, and wherein said spiral scanning is conducted around an axial direction, and wherein the step of for controlling the spiral scanning comprises setting said pitch value dependent on said ECG signal for obtaining a gap-free image of the heart in the axial direction.

10. A method as claimed in claim 8 wherein the step of for controlling said spiral scanning includes storing said ECG signal along a time axis, and marking a beginning of the spiral scanning on said time axis for correlating said spiral scanning with said ECG signal.

11. A method as claimed in claim 10 wherein the stored ECG signal exhibits a plurality of successive, predetermined time windows along said time axis, and wherein the step of controlling said spiral scanning comprises obtaining said spiral scan data only during said time windows, with only one of said datasets being obtained per time window.

12. A method as claimed in claim 11 wherein the step of conducting spiral scanning comprises rotating a radiation source and a radiation detector around said examination volume in a plurality of successive revolutions, and wherein the step of controlling said spiral scanning comprises obtaining data in said time windows which are respectively portions of successive revolutions of said spiral scanning.

13. A method as claimed in claim 11 wherein the step of producing said overall image comprises producing said overall image from datasets obtained at equidistant time intervals.

14. A method as claimed in claim 8 wherein the steps of conducting a spiral scanning comprises rotating a radiation source and a radiation detector around an axis while advancing a patient bed along said axis at a bed speed, and wherein said spiral scanning has a pitch value associated therewith, and wherein said method comprises the additional step of monitoring a heartbeat frequency of the heart during said spiral scanning and controlling said bed speed so that a predetermined pitch value is not exceeded.

* * * * *